US009283212B2

(12) United States Patent
O'Neil

(10) Patent No.: US 9,283,212 B2
(45) Date of Patent: Mar. 15, 2016

(54) PHARMACEUTICAL PREPARATION AND DELIVERY SYSTEM

(75) Inventor: Alexander George Brian O'Neil, West Lothian (AU)

(73) Assignee: PALMAYA PTY LTD, Subiaco, Western Australia (AU)

( * ) Notice: Subject to any disclaimer, the term of this patent is extended or adjusted under 35 U.S.C. 154(b) by 0 days.

(21) Appl. No.: 13/202,402

(22) PCT Filed: Feb. 19, 2010

(86) PCT No.: PCT/AU2010/000186
§ 371 (c)(1),
(2), (4) Date: Jan. 5, 2012

(87) PCT Pub. No.: WO2010/094074
PCT Pub. Date: Aug. 26, 2010

(65) Prior Publication Data
US 2012/0122851 A1 May 17, 2012

(30) Foreign Application Priority Data

Feb. 20, 2009 (AU) ................................ 2009900741

(51) Int. Cl.
*A61K 31/437* (2006.01)
*A61K 31/4745* (2006.01)
*A61K 31/5517* (2006.01)

(52) U.S. Cl.
CPC ............ *A61K 31/437* (2013.01); *A61K 31/4745* (2013.01); *A61K 31/5517* (2013.01)

(58) Field of Classification Search
USPC .......................................................... 514/221
See application file for complete search history.

(56) References Cited

U.S. PATENT DOCUMENTS

| 3,523,906 | A | 8/1970 | Vrancken |
| 4,962,128 | A | 10/1990 | Doogan |
| 7,348,321 | B2 | 3/2008 | Ibanez |
| 2008/0207601 | A1* | 8/2008 | Sabnani ........................ 514/221 |

FOREIGN PATENT DOCUMENTS

| WO | 9529678 A1 | 11/1995 |
| WO | 0217971 A1 | 3/2002 |
| WO | 03079976 A2 | 10/2003 |
| WO | 2006110557 A2 | 10/2006 |
| WO | 2009016329 A1 | 2/2009 |

OTHER PUBLICATIONS

O'Neil et al. "Rapid benzodiazepine withdrawal as an out-patient procedure" (uki.net/php/files/staplefordpages.uki.net/resources/Stapleford_flum_fina.pdf) (Mar. 2006).*
Schuerholz et al. "Ringer's solution . . . ", British Journal of Anesthesia 92 (5): pp. 716-721 (2004).*

(Continued)

*Primary Examiner* — Ernst V Arnold
*Assistant Examiner* — Kyung Sook Chang
(74) *Attorney, Agent, or Firm* — Fredrikson & Byron P.A.

(57) ABSTRACT

The present invention relates to unique delivery systems and the use of an imidazobenzodiazepine derivative, such as flumazenil either alone or in combination with other receptor antagonists in the treatment of disease or medical disorders.

12 Claims, 4 Drawing Sheets

(56) References Cited

OTHER PUBLICATIONS

Pharmaceutical Partners of Canada Inc. (total pages of 2): "Flumazenil Injection, USP", Dec. 31, 2008, XP55031164, Retrieved from Internet: http:I/ppcdrugs.com/en/productslproduct_inserts/EN_WebInse~_Flumazenil.pdf (of record).*

Chern et al., "Continuous Flumazenil Infusion in Preventing Complications Arising From Severe Benzodiazepine Intoxication", American Journal of Emergency Medicine, vol. 16, No. 3, May 1998, 238-241.

Sittl et al., "Analgesic Efficacy and Tolerability of Transdermal Buprenorphine in Patients with Inadequately Controlled Chronic Pain Related to Cancer and Other Disorders: A Multicenter, Randomized, Double-Blind, Placebo-Controlled Trial", Clinical Therapeutics, Jan. 2003, vol. 25, No. 1, 150-168.

Pharmaceutical Partners of Canada Inc.: "Flumazenil Injection, USP", Dec. 31, 2008, XP55031164, Retrieved from Internet: URL:http://ppcdrugs.com/en/products/product_inserts/EN_WebInsert_Flumazenil.pdf [retrieved on Jun. 26, 2012].

European Search Report and Written Opinion dated Apr. 7, 2012 for related European Application No. 10743330.2, 13 pgs.

Coupland, et al., "Flumazenil Challenge in Social Phobia", Depression and Anxiety 11:27-30 (2000).

Potokar, et al., "Flumazenil in Alcohol Withdrawal: A Double Blind Placebo-Controlled Study", Alcohol & Alcoholism, vol. 32, No. 5, pp. 605-611, 1997.

Bell, et al., "Does 5-HT restrain panic? a tryptophan depletion study in panic disorder patients recovered on paroxetine", J. of Psychopharmacology 16(1) (2002) 5-14.

* cited by examiner

PHARMACEUTICAL PREPARATION AND DELIVERY SYSTEM

CROSS-REFERENCE TO RELATED APPLICATIONS

The present application claims priority to International Application No. PCT/AU2010/000186 filed Feb. 19, 2010, which in turn claims priority to AU Application No. 2009900741 filed Feb. 20, 2009, the teachings of which are incorporated herein by reference.

FIELD OF THE INVENTION

The present invention relates to unique delivery systems and the use of an imidazobenzodiazepine derivative, such as flumazenil either alone or in combination with other receptor antagonists in the treatment of disease or medical disorders.

BACKGROUND ART

Flumazenil was first synthesised in 1979 and is an example of an imidazobenzodiazepine derivative. Its pKA value in weak base is 1.7. Flumazenil is a basic drug and insoluble in water, but slightly soluble in acidic aqueous solutions. For example, the solubility of flumazenil at pH 1.2 is 3 mg/ml and at pH 7.5, flumazenil has a solubility of only 0.6 mg/ml. The drug has a well established place in the treatment of benzodiazepine overdose as it has been commercially available as an intravenous injection containing 5 or 10 ml aqueous solution (0.5 g/ml at pH 4).

Flumazenil reverses the effects of benzodiazepines by competitive inhibition at the benzodiazepine binding site on the $GABA_A$ receptor. In addition, intravenous administration of flumazenil may also be effective in overdoses of non-benzodiazepine sleep enhancers in high short term doses, and has been used in hepatic encephalopathy, though results have been mixed.

The onset of action of intravenous delivery of flumazenil is rapid and usually effects are seen within one to two minutes. The peak effect is seen at about six to ten minutes. In general, the recommended dose for adults is an intravenous dose of 200 μg every one to two minutes until the effect is seen, to a maximum of 3 mg per hour. Since many benzodiazepines have a longer half life than flumazenil, repeated doses of flumazenil may be required to prevent recurrent symptoms of over-dosage. Furthermore, patients that are physically dependent on benzodiazepines may suffer benzodiazepine withdrawal symptoms, including seizure, upon administration of flumazenil.

It is commonly known that flumazenil is a weak partial agonist in some animal models of activity, but has little or no agonist activity in humans. Furthermore, it has been suggested that flumazenil does not antagonise the central nervous system effects of drugs affecting GABA neurons by means other than the benzodiazepine receptor (including ethanol, barbiturates, or general anesthetics) and does not reverse the effects of opioids.

Bolus infusion of flumazenil of 2 mg in 10 minutes can act as a specific panicogen in subjects with panic disorder [Bell C et al., (2000). Does 5-HT restrain panic? A tryptophan depletion study in panic disorder patients recovered on paroxetine. *J. Psycho-pharmacol.* 16: 5-14] However, intravenous infusion of flumazenil has no effect on social anxiety [Coupland N J et al., (2000). Flumazenil challenge in social phobia. *Depress Anxiety.* 11:27-30] or alcohol-dependent subjects [Potokar J et al., (1997). Flumazenil in alcohol withdrawal: a double-blind placebo-controlled study. *Alcohol Alcohol.* 32: 605-611].

One of the problems associated with the treatment of patients in need of flumazenil is compliance and the difficulties associated with intravenous infusion. That is, the very short half life and low oral bioavailability of the compound limit the use of flumazenil to clinical settings, such as hospitals and drug clinics, which are often avoided by patients in need of treatment. Furthermore, venous access may be compromised due to the patient's state of physical health. Therefore, there exists a need to treat diseases or medical disorders in a less invasive manner.

The applicant of the present invention has surprisingly found that low doses of imidazobenzodiazepine derivatives, such as flumazenil alone or in combination with receptor antagonists have unexpected effects on the central nervous system. In addition, a method for the administration of flumazenil alone or in combination with antagonists has been developed which allows for a patient to be treated either on a patient controlled basis or over a continuous period of time via subcutaneous administration.

SUMMARY OF THE INVENTION

The applicant has surprisingly found that a solution of flumazenil at a concentration of between 0.11 to 0.7 mg/ml may be prepared in saline at a pH between pH 6.5 to 7.0 for the subcutaneous administration or patent controlled delivery to a subject in need of treatment thereof.

In addition, the applicant has surprisingly found that the infusion or the implant of a low dose of an active agent delivered in a continuous and subcutaneous delivery system over an extended period of time of greater than four days has advantages over the intravenous or oral administration of the active agent.

Furthermore, applicant has found that a patient controlled delivery system which administers an active agent such as flumazenil or a benzodiazepine antagonist has beneficial effect in the treatment of disorders, addictions and/or disease. The active agent may be delivered intermittently in a bolus dose across the nasal membrane (trans-nasally) either alone or in combination with one or more antagonists and has been shown to have beneficial effects in the treatment of disorders, addictions and/or disease. Furthermore, the active agent may be delivered intermittently and subcutaneously via the use of a patent controlled pump. Alternatively, the active agent may be delivered transcutaneously across the skin, such as via a patch or cream. In a highly preferred embodiment, the active agent if flumazenil or a benzodiazepine antagonist.

In one aspect of the present invention there is provided a preparation of flumazenil at a concentration of between 0.11 to 0.7 mg/ml prepared in saline at a pH between pH 6.5 to 7.0 for the subcutaneous administration or patent controlled delivery to a subject in need of treatment thereof. It is anticipated that other benzodiazepine antagonists may also be used instead of flumazenil.

In a further aspect of the present invention there is provided a preparation of flumazenil or benzodiazepine antagonist at a concentration of between 0.11 to 0.7 mg/ml prepared in saline at a pH between pH 6.5 to 7.0 when used in the continuous or patient controlled subcutaneous delivery of flumazenil or benzodiazepine antagonist to control anxiety and/or offer a means of gradually correcting anxiety disorders In a further aspect of the present invention there is provided a pharmaceutical preparation comprising an active agent administered at a continuous rate of about 40 μg/h to about 1000 µg/h over a sustained period of time of greater than four days to a subject in need of treatment thereof. In a highly preferred embodiment, the active agent is an imidazobenzodiazepine derivative, such as flumazenil or benzodiazepine antagonist.

In another aspect of the present invention there is provided a pharmaceutical preparation comprising an active agent administered via a patient controlled system, such as a pump, nasal spray or patch to a subject in need of treatment thereof. In a highly preferred embodiment, the active agent is an imidazobenzodiazepine derivative, such as flumazenil or a benzodiazepine antagonist.

In one embodiment of the present invention the pharmaceutical preparation may optionally comprise one or more additional active agent(s).

In another aspect of the present invention there is provided a delivery system for administering a pharmaceutical preparation comprising an active agent comprising the step of subcutaneously administering at a continuous rate of about 40 µg/h to about 1000 µg/h of the active agent over a sustained period of time of greater than four days to a subject in need of treatment thereof.

In another embodiment of the present invention, the delivery system provides for the administration of a pharmaceutical preparation comprising one or more additional active agent(s).

In a further aspect of the present invention there is provided a pharmaceutical preparation for the self administration of a bolus dose of an active agent administered to the subject in need thereof by the subject.

In yet a further aspect of the present invention there is provided a kit comprising a preparation of flumazenil or benzodiazepine antagonist at a concentration of 0.11 mg/ml to 0.7 mg/ml prepared in saline at a pH between 6.5 to 7; and optionally one or more additional active agent(s) and instructions for the use of the pharmaceutical preparation. The kit may further contain a means for administration of the pharmaceutical preparation.

DISCLOSURE OF THE INVENTION

General

Figure 1:
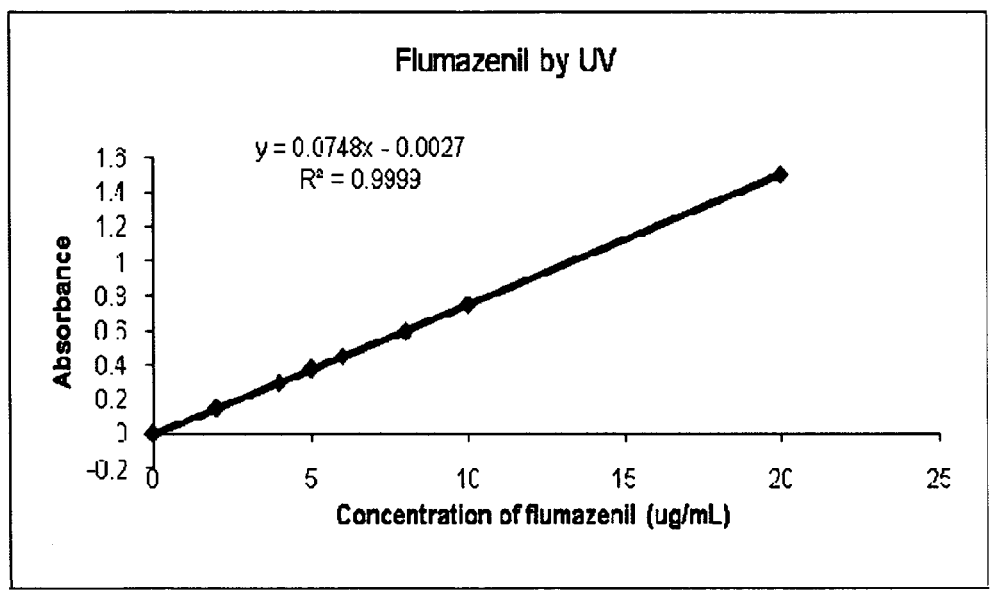
FIG. 1: Graphical representation of a standard curve of the concentration of flumazenil solution measured at a wavelength of 460 nm.

Those skilled in the art will appreciate that the invention described herein is susceptible to variations and modification other than those specifically described. It is to be understood that the invention includes all such variations and modification. The invention also includes all of the steps, features, compositions and compounds referred to or indicated in the specification, individually or collectively and any and all combinations or any two or more of the steps or features.

The present invention is not to be limited in scope by the specific embodiment or examples described herein, which are intended for the purpose of exemplification only. Functionally equivalent products, compositions and methods are clearly within the scope of the invention as describe herein.

The entire disclosures of all publications (including patents, patent applications, journal article, laboratory manuals, book or other documents) cited herein are hereby incorporated by reference. No admission is made that any of the references constitute prior art or are part of the common general knowledge of those working in the field to which this invention relates.

Throughout the specification and claims, unless the context requires otherwise, the word "comprise" or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The term "active agent" refers to a compound useful for effecting some beneficial change in the subject to which it is administered. For example, "active agents" within the scope of this definition include imidazobenzodiazepine derivatives, benzodiazepine antagonists, flumazenil, opioid antagonists, cannabanoid antagonists, and naltrexone.

The term "effective amount" as applied to "one or more active agents" refers to that amount which is sufficient to effect the desired change in the subject. It is within the knowledge and skill of a person skilled in the art to determine the effective amount of an active agent.

By "microcapsules" is meant particles that contain an active agent dispersed or dissolved within a biodegradable, biocompatible polymer that serves as the matrix of the particle.

By "biodegradable" is meant a material that should degrade by bodily processes to products readily disposable by the body and should not accumulate in the body. The products of the biodegradation should also be biocompatible with the body.

By "biocompatible" is meant not toxic to the human body, is pharmaceutically acceptable, is not carcinogenic, and does not significantly induce inflammation in body tissues.

The term "treatment" as used herein covers any treatment of a disease in an animal (including a human), and includes: (i) preventing the disease from occurring; (ii) inhibiting the disease, i.e., arresting its development; (iii) relieving the disease, i.e., causing regression of the disease; or (iv) modifying normal biological activity such as in the case of cravings, promotion of weight gain or contraception.

While the pharmaceutical preparations prepared herein may be administered in any form, preferably they are adapted for drug delivery beneath subcutaneous tissue, including subcutaneous infusion or subcutaneous implants. The pharmaceutical preparations may also be administered as a spray to the mucosal or oral membranes.

The term 'implant(s)' refers to any object that may be required to be administered to a patient for a pharmaceutical effect including the pharmaceutical preparation of the present invention. For the purposes of this specification, the term 'implant(s)' refers to a pharmaceutical preparation comprising an active agent. In a preferred embodiment, the implant comprises at least flumazenil or an imidazobenzodiazepine derivative as the active agent.

The term 'disorders' as used herein covers any medical disorders such as but not limited to: sleep disorders, cognitive function disorders, smoking disorders, alcohol disorders, benzodiazepine disorders, gambling disorders, antipsychotic medication withdrawal, non-drug related anxiety disorders, amphetamine addiction, cocaine addiction, opiate addiction, cannabis dependency, addictive substance dependency and withdrawal states, and any disorders associated with addictive substance dependency. In general these disorders are a result of a state of anxiety.

The term 'anxiety' includes anxiety as a result of cravings for addictive substances, withdrawal from addictive substances and non-drug related anxiety disorders.

The pharmaceutical preparation of the present invention may be administered to any mammal. Preferably, the mammal is a human being.

DETAILED DESCRIPTION OF THE INVENTION

Previous methods of treating disorders, diseases or drug addictions and associated problems have utilised the intravenous injection of antagonists. Flumazenil is one antagonist that has been used in the treatment of benzodiazepine addiction. However, flumazenil has been shown to have no beneficial effects on treating anxiety, cravings or various other conditions.

A solution of flumazenil in saline has been prepared from commercially available flumazenil. The applicant has found that this solution is suitable in the subcutaneous administration of flumazenil via continuous subcutaneous infusion or in the preparation of a subcutaneous implant. In a further embodiment, flumazenil may be administered to a subject in need thereof via patient controlled delivery systems such as pumps, nasal spray devices or patches.

In one embodiment of the present invention, there is provided a solution of flumazenil prepared at a concentration of between about 0.11 mg/ml to 0.7 mg/ml in saline at a pH of between 6.5 to 7.0. The flumazenil solution of the present invention is prepared at a concentration five times the amount previously used to treat subjects. Furthermore, the pH has been adjusted to a value that is suitable for subcutaneous administration to subjects. To the best of the applicant's knowledge a concentrated solution of flumazenil at this pH has never before been used in the treatment of a subject.

In a highly preferred embodiment the solution of flumazenil or benzodiazepine antagonist is between about 0.2 mg/ml to 0.7 mg/ml. In another embodiment the solution of flumazenil or benzodiazepine antagonist is between about 0.3 mg/ml to 0.6 mg/ml. In yet another embodiment, the solution of flumazenil or benzodiazepine antagonist is between about 0.4 mg/ml to 0.6 mg/ml. In still a further embodiment of the present invention the solution of flumazenil or benzodiazepine antagonist is 0.53 mg/ml.

The solution of flumazenil or benzodiazepine antagonist at a concentration of 0.11 mg/ml to 0.7 mg/ml and preferably 0.53 mg/ml prepared in saline at a pH between 6.5 to 7.0 is effective in the control of anxiety and offers a means of gradually correcting anxiety disorders when administered subcutaneously for a continuous period of time or when administered by a patient controlled delivery system.

The subcutaneous infusion or the implant of a pharmaceutical preparation comprising an active agent, such as an imidazobenzodiazepine derivative (e.g. flumazenil or a benzodiazepine antagonist) delivered in a continuous system over an extended period of delivery time of greater than four days has advantages over the intravenous or oral administration of the imidazobenzodiazepine derivative.

In one embodiment, the present invention provides a pharmaceutical preparation comprising an active agent administered at a continuous rate of about 40 µg/h to about 1000 µg/h over a sustained period of time of greater than four days to a subject in need of treatment thereof. In a preferred embodiment, the active agent is an imidazobenzodiazepine derivative. In a highly preferred embodiment, the active agent is flumazenil or a benzodiazepine antagonist.

In another embodiment of the present invention, there is provided a pharmaceutical preparation comprising an active agent administered at a continuous rate of about 40 µg/h to about 1000 µg/h over a sustained period of time of greater than four days to a subject in need of treatment thereof, wherein the pharmaceutical preparation is administered via the subcutaneous route. In a preferred embodiment, the active agent is an imidazobenzodiazepine derivative.

In a highly preferred embodiment, the active agent is flumazenil or a benzodiazepine antagonist.

In another embodiment the pharmaceutically preparation optionally includes one or more additional active agent(s). The addition of one or more active agents results in a synergistic effect, whereby the additional active agent results in an increased effect over the effect of the imidazobenzodiazepine derivative alone. Further active agent(s) that are antagonists, include but not limited to opioid and cannabanoid antagonists and in the case of opioid antagonists these independently decreased smoking cravings when administered in a patent controlled administration model. An example of such an antagonist is naltrexone.

In another preferred embodiment, the flumazenil preparation of the present invention may be administered to a subject in need thereof via a patient controlled delivery system. In one embodiment the patient controlled delivery system is a pump. A person skilled in the art would be familiar with such patient controlled devices. The pump is designed to deliver a predetermined dose of flumazenil via the subcutaneous route, when required by the patient. In a highly preferred embodiment, the dose of flumazenil delivered to the patient is about 20 µg to about 1000 µg.

In another preferred embodiment of the present invention, the flumazenil (or benzodiazepine antagonist) preparation of the present invention may be delivered across the nasal membrane (trans-nasally) to a subject in need thereof by nasal spray delivery device. A person skilled in the art would be familiar with the types of nasal spray devices for use in delivering the flumazenil or benzodiazepine antagonist. In a highly preferred embodiment, the individual dose of flumazenil or benzodiazepine antagonist per delivery is between about 20 µg to 1000 µg and preferably 200 µg.

In another preferred embodiment of the present invention the flumazenil or benzodiazepine antagonist preparation of the present invention is delivered to a subject in need thereof via a patch. The patch is designed to deliver an amount of flumazenil or benzodiazepine antagonist between about 20 µg to about 1000 µg to a subject over an extended period of time.

Additional active agents may also be added to the flumazenil or benzodiazepine antagonist preparation of the present invention when used in the patient controlled delivery systems described above. The addition of one or more active agents results in a synergistic effect, whereby the additional active agent results in an increased effect over the effect of the imidazobenzodiazepine derivative alone. Further active agent(s) that are antagonists, include but not limited to opioid and cannabanoid antagonists and in the case of opioid antagonists these independently decrease smoking cravings when administered in a patent controlled administration model. An example of such an antagonist is naltrexone There have been attempts in the past to use flumazenil to decrease benzodiazepine dependence with infusion rates at a minimum of 250 µg/h given in a hospital setting with intravenous infusions [Gerra G et al., (2002). Intravenous flumazenil versus oxazepam tapering in the treatment of benzodiazepine withdrawal: a randomized, placebo-controlled study. *Addiction Biology*, 7, 385-395]. In most patients with benzodiazepine dependence patients have poor venous access, are not available for hospital infusions, or are not able to keep venous access open for long enough and many relapse back on to benzodiazepines once the intravenous infusion stops. Intravenous infusions are not conducted for longer than four days, mainly due to the limitations of the clinic opening hours, patient compliance and the difficulty in maintaining an intravenous infusion for extended periods of time.

The value of delivering flumazenil subcutaneously in an amount of 40-1000 µg/h continuously for a period of time greater than four days at levels that probably only saturate 1-2% of the receptors, has not previously been appreciated. Without being limited by theory, the applicant believes the unique value of long or medium term delivery of flumazenil at this 1-2% receptor saturation rate is associated with decreasing receptor tolerance or increasing receptor sensitivity gradually at the cellular level and has not previously been appreciated by the person skilled in the art.

In one embodiment, the present invention provides a pharmaceutical preparation comprising an active agent administered subcutaneously at a continuous rate of about 40 µg/h to 1000 µg/h to a subject in need of treatment thereof over an extended period of delivery time of greater than four days. In a preferred embodiment, the amount of active agent is administered at a continuous rate of between about 80 µg/h to 250 µg/h.

In one embodiment the active agent is an imidazobenzodiazepine derivative. In a highly preferred embodiment, the imidazobenzodiazepine derivative is flumazenil or a benzodiazepine antagonist.

When the active agent is flumazenil, the amount of flumazenil delivered ranges from about 40 µg/h to 1000 µg/h for a period of greater than four days. Preferably the amount of flumazenil delivered is less than 1000 µg/h. In a highly preferred embodiment, the amount of flumazenil delivered is between 80 µg/h to 250 µg/h.

The present invention relates to the surprising finding that extended subcutaneous delivery of active agent (such as flumazenil) below 1000 µg/h was found to be efficient for control of benzodiazepine dependence and other medical disorders associated with addiction or medical disorders not associated with addiction. These medical disorders include but are not limited to: decreased anxiety, decreased sedation, increased cognitive function, improvement in sleep disorders, anxiety control to a level long term antipsychotic medications could also be stopped, an improvement in patients with chronic depression, a decrease in craving for alcohol, smoking, and amphetamines.

In one embodiment of the present invention the active agent is continuously and subcutaneously delivered for a period of time of greater than four days to six months. In a preferred embodiment, the active agent is continuously and subcutaneously delivered for a period of 16 days to six months. In a highly preferred embodiment of the present invention, the active agent is continuously and subcutaneously delivered for a period of at least five weeks to nine weeks.

A person skilled in the art would appreciate that the total duration of delivery of the active agent is dependent on the subject's response to the treatment and the nature of the disease, medical disorder or addiction to be treated. For example, a patient requiring treatment for long term benzodiazepine dependence may require an initial subcutaneous and continuous administration of flumazenil, followed by one or more further treatments with flumazenil according to the present invention to completely treat the dependency to benzodiazepine.

In one embodiment of the present invention, the active agent may be delivered in the form of an implant. Preferably, the length of time which the implant can deliver active agent is for more than four days. More preferable is a duration of delivery of 16 days or more. Another preferred duration of delivery is over 21 days. Another preferred duration of delivery is over 30 days. More preferable is a duration of delivery of over 40 days. More preferable is a duration of delivery of over 50 days. More preferable is a duration of delivery of over three months. Still another preferable duration of delivery is over six months. A preferred embodiment is a pharmaceutical composition comprising flumazenil having a lifespan of more than four days, more preferably about 16 days, more preferably more than 21 days, more preferably more than 30 days, more preferably more than 40 days more preferably more than three months or 100 days, and still more preferably over six months.

In an alternate embodiment of the present invention more than one implant may achieve the continuous and subcutaneous delivery of the active agent to the subject. For example, a first implant delivering the active agent in a continuous and subcutaneous manner may be administered to the subject wherein the active agent is released for a period of time. A second implant of the same active agent may then be administered towards the end of the life time of the first implant to maintain the continuous and subcutaneous delivery of the active agent for a further period of time. A third implant of the same active agent may be administered to maintain the delivery of the active agent, for a further period of time, and so on, thereby completing the administration of a continuous and subcutaneous delivery of active agent over the required period of time to treat the patient.

In one embodiment, the present invention provides an apparatus for the subcutaneous and continuous administration of an active agent. In a preferred embodiment of the present invention there is provided a pump which delivers a preset amount of active agent.

For example, a pump capable of subcutaneous and continuous administration of an active agent may be loaded with a required dosage of active agent. The pump is then connected to appropriate tubing and via the subcutaneous route, the active agent is administered into a patient for a predetermined period of time. The pump system may then be reloaded with active agent to maintain the subcutaneous administration of active agent.

The method of the present invention is not limited to the administration of the active agent via just implant or just subcutaneous infusion. That is, a combination of subcutaneous infusion and implants may be used to best treat the subject. For example, the subject may be administered an effective amount of active agent via subcutaneous administration for the initial treatment, followed by a period of treatment with implantable active agent for the remainder of the treatment or vice versa.

Patient controlled delivery systems appear promising to treat disease, disorders, addictions, control symptoms and/or correct anxiety disorders when they occur. For this reason, a subcutaneous flumazenil or benzodiazepine antagonist delivery on an outpatient basis was developed to give long term control of addiction such as benzodiazepine dependence, by administration of flumazenil or a benzodiazepine antagonist when required. Furthermore, applicant has found that patient controlled drug delivery systems are suitable to treat disorders not associated with addiction, such as anxiety. The delivery of flumazenil or a benzodiazepine antagonist may occur via subcutaneous delivery (e.g, a patient controlled pump), trans-nasally (e.g. via a nasal spray across the nasal membrane) or transcutaneously (e.g. across the skin via a patch).

Thus, the present invention describes new outpatient techniques of delivering flumazenil (or related imidazobenzodiazepine derivative or benzodiazepine antagonist) using subcutaneous delivery methods and patient controlled methods using micro-doses (between about 20 μg to 1000 μg bolus size or 40-1000 μg/h) previously regarded as non therapeutic for a number of conditions where no previous claim for benefits has been observed.

A of active agent, such as flumazenil or a benzodiazepine antagonist administered in a bolus and intermittent or pulsitile dose across the nasal membrane, when required has been shown to reduce cravings for nicotine and other addictive substances.

In a further embodiment, the present invention provides a pharmaceutical preparation comprising a micro-dose of flumazenil (or a benzodiazepine antagonist) either alone, or combined with a micro-dose of another active agent, such as an opioid or cannabanoid antagonist administered across the nasal membrane for the treatment of disorders and/or non-drug related anxiety. In a preferred embodiment, the amount of flumazenil or benzodiazepine antagonist is in the order of about 20 μg to about 200 μg. In another preferred embodiment the amount of flumazenil is about 50 μg. When the pharmaceutical preparation comprises another opioid or a cannabanoid antagonist, the amount of the additional active agent is in the order of about 20 μg to about 200 μg. In another preferred embodiment the amount of additional active agent is about 50 μg.

In one example, the above preparation is useful in the treatment of craving for smoking cigarettes and marijuana. When the active agents are administered together, applicant observed the subject's response to be greater than for opioid antagonist alone or flumazenil alone. Thus, the author observed a synergistic effect which controlled symptoms. To the author's knowledge, these findings have not previously been reported.

In general, subjects treated with the pharmaceutical preparation of the present invention exhibited the following new observations after a subcutaneous and continuous administration of flumazenil or a patent controlled administration of flumazenil either alone or in combination with one or more active agents:

1. Subcutaneous delivery of flumazenil is safe, practical and efficient at maintaining consistent active agent delivery, in order to achieve clinical effects not seen before;
2. The low dose of flumazenil in saline, prepared at a suitable pH value, allows for delivery of the active agent as a subcutaneous infusion or as a subcutaneous implant; and
3. Neither the subcutaneous infusion nor the implant (i.e. subcutaneous delivery) of flumazenil has been used before, as subcutaneous delivery was not previously recognised as being advantageous. The value of continuous delivery of 40-1000 μg/h continuously over greater than four days at levels that probably only saturate 1-2% of the receptors were not previously appreciated. We believe the unique value of long or medium term delivery of flumazenil at this 1-2% receptor saturation rate is associated with decreasing receptor tolerance or increasing receptor sensitivity gradually at the cellular level.

The subcutaneous delivery of flumazenil or a benzodiazepine antagonist alone or in combination with other active agents provides a treatment for at least the following disorders: anxiety disorders (both drug and non-drug related), addiction disorders, sleep disorders, cognitive function disorders, liver failure patients with cognitive function disorders where daily continuous long term delivery of flumazenil is used, patients with neurological disorders such as Parkinson's disease, and epilepsy.

As mentioned above, the drug delivery system of the present invention is useful for treating a number of diseases and disorders, especially disorders related to addiction. Patients requiring treatment using standard amounts and methods of treatment with flumazenil or benzodiazepine antagonist or other imidazobenzodiazepine derivatives, are within the scope of the invention. In addition, patients suffering from decreased cognitive function, particularly relating to those subjects who use benzodiazepines. However, other groups of subjects with decreased cognitive function can also benefit with this new delivery system, including but not limited to subjects with hepatic dysfunction, respiratory dysfunction and some forms of brain injury. Other disorders that may be treated with the present invention include chronic anxiety disorders, sleep disorders, drug withdrawal states, smoking disorders (e.g. nicotine dependence), benzodiazepine dependence, alcohol dependence, amphetamine dependence, and opioid dependence.

In relation to addiction disorders, the pharmaceutical preparation and the administration thereof according to the present invention may be useful in the treatment of a subject who may be showing signs of or who is addicted to compounds, such as but not limited to: cannabinoids (such as hashish and marijuana), depressants (such as barbiturates, benzodiazepines, gamma-hydroxybutyrates, and methaqualiones), dissociative anaesthetics (such as ketamine and phencyclidine & analogues), hallucinogens (such as lysergic acid diethylamide [LSD], mescaline and psilocybin), opioid and morphine derivatives (such as codeine, fentanyl & analogues, heroin, morphine, opium, oxycodone HCL, hydrocodone, bitartrate, and acetaminophen), stimulants (such as amphetamines, cocaine, methylene dioxymethamphetamine, methylphenidative, nicotine), anabolic steroids, dextromethorphan, and inhalants (such as solvents, gases, nitrites, laughing gas, poppers, snappers and whippets).

When treating drug withdrawal states, the delivery system of the present invention has advantages over the previously known treatment methods. Flumazenil at low dose rates (less than 1000 μg/h) by subcutaneous delivery or prolonged infusion methods (greater than fours days to weeks or months) or patient controlled delivery systems (such as patient controlled bolus doses titrated against symptoms) appear useful in withdrawal symptoms such as smoking, alcohol, cannabis, benzodiazepines, amphetamines, opiates and other dependency inducing drugs.

Anxiety may result from a number of factors. That is, anxiety is associated with addiction to substances, withdrawal from drug dependency and from non-drug related causes. The preparation of the present invention and the delivery systems of the present invention provides a useful treatment of all forms of anxiety, regardless of the cause of the anxiety.

In a further aspect of the present invention there is provided a method for the treatment of a disease or disorder comprising the subcutaneous administration of an active agent at a continuous rate of about 40 μg/h to about 1000 μg/h over a period of time of greater than four days to a subject in need of treatment thereof.

The present invention is also provides a method for the patient controlled delivery of flumazenil or a benzodiazepine antagonist in the treatment of a disease or disorder. In one embodiment, the method comprises the administration of an active agent across the nasal membrane at a dose of about 20 μg to about 200 μg of active agent to a subject in need of treatment thereof. In a highly preferred embodiment, the dose is self administered by the subject at the onset of craving for an addictive substance. In a highly preferred embodiment, the addictive substance is nicotine, marijuana or alcohol. In another embodiment, the dose is self administered by the subject at the onset of a feeling of anxiety.

In another embodiment, the present invention provides a method comprising the subcutaneous administration of an active agent at a dose of about 200 μg to 1 mg of active agent to a subject in need of treatment thereof. In a highly preferred embodiment, the dose is self administered by the subject at the onset of craving for an addictive substance or for the treatment of anxiety.

A person skilled in the art would appreciate that a patch delivering an amount of flumazenil to maintain a rate of between 40 μg/h to 1000 μg/h could also be used in the treatment of a subject in need thereof.

EXAMPLES

The experiments conducted as described below have shown that the production of flumazenil in a dilution of about 12 to 16 mg flumazenil per 30 mL of saline solution produce a solution suitable for the subcutaneous administration when placed in a spring driven 30 mL pump.

A solution of flumazenil in saline solution was prepared by dissolving 16 mg of flumazenil in 30 mL of saline and adjusting the pH to between 6.5 to 7.0 with a phosphate buffer, solution (pH 5.0). The final concentration of flumazenil in saline is 0.53 mg/mL.

For example, to a 100 mL measuring flask, 53 mg (accurately weighed) of flumazenil powder was added to 60 mL saline solution, the final pH was adjusted to between 6.5 to 7.0 using phosphate buffer solution pH 5.0. Then the solution was made up to a total of 100 mL using water. The flumazenil concentration was confirmed by HPLC analysis (see FIG. 1).

Subcutaneous Infusion

A solution of flumazenil in saline was prepared as set out above. That is, a portion of 12 to 16 mg flumazenil in 30 mL of saline was prepared for the subcutaneous administration via a spring driven 30 mL pump. The pump used was a portable infusion Springfusor pump (O'Neil Balloon Infuser, ID: SBI-100; Go Medical Industries). The delivery rate of the flumazenil was in the order of 40 to 1000 μg/h.

The use of this dosage of flumazenil over a continuous period of time using a delivery pump, such as the Springfusor pump provides a continuous low dose of flumazenil which has the benefit of overcoming the need for an intravenous line and the problems associated with clinical administration of the active agent.

Patient Treatment—Case Study

A patient with an addiction to benzodiazepine drugs and other addictive substances agreed to accept a subcutaneous dose of flumazenil administered at a rate of 166 μg/h for greater than four days.

A Springfusor pump connected to tubing and a butterfly cannula was set up, wherein the pump was loaded with 30 mL of flumazenil solution (0.53 mg/mL). The butterfly cannula was inserted into the patient's abdomen using standard techniques and the pump set to delivery flumazenil at a rate of 166 μg/h. After the initial four day (96 hour) administration, the pump was reloaded with a further 30 mL of flumazenil solution (0.53 mgmL) and delivery continued for a further four days (96 hours). The subcutaneous infusion continued for a total of three weeks.

During the treatment period, the patient reported that the continuous subcutaneous infusion was less invasive that an IV infusion as she was not required to attend a clinic for the daily intravenous infusions of flumazenil and the subcutaneous infusion system was more robust that an IV system. In addition, the patient was only required to briefly return to the clinic to top up the dosage of flumazenil, and such, could be treated as an outpatient.

The patient reported the benefits of low dose flumazenil after four days and the progressive improvement over the following five to six weeks. She also reported better sleep patterns and her dependency on anti-psychotic drugs decreased over the time of the subcutaneous infusion delivery, and eventually she was not dependent on these drugs. Her cravings for alcohol and smoking also decreased and eventually were considered negligible both during infusion and after completion of the six week period of flumazenil delivery. The patient had previously suffered from panic attacks, which she recorded as gone after her full treatment with subcutaneous flumazenil infusion. The patient also reported a change in mood and improved cognitive functions, including, clear thinking, better judgement and improved relationships with family and friends.

The new delivery system allows the delivery of 30 mL solution containing 16 mg of flumazenil at a rate above 4 mg/day (166 μg/h) for up to four days. This constant delivery of 166 μg/h appears to be effective as an anticonvulsant whereas intravenous infusions below 80 μg/h have failed to stop epileptic convulsions. Since oral administration of flumazenil is less successful as an anticonvulsant it has been proposed that consistent delivery of flumazenil at a rate above 80 μg/h would be more appropriate.

The constant infusion of flumazenil at the above rates was unexpectedly associated with the following observations:

a) Craving for cigarettes, alcohol, amphetamines, opiates and benzodiazepines was reduced during the time of the infusion and a reduction in craving continued for a considerable time after the infusion stopped.

b) Anxiety levels in response to many stimuli were reduced during the time of the infusion. This was unexpected as previous publications comment on the onset of acute panic attacks on injection of flumazenil.

c) Patients with chronic sleep disorders gradually improved each day the infusion was continued. We believe this may not have been observed before as long term infusions have not been practiced.

d) Cognitive function appeared to improve daily in the first two weeks of the infusion especially in patients with addictions. As long term infusions have not been practiced this also has not been clinically recorded.

The delivery of flumazenil through subcutaneous infusions has previously not been described. In human subjects with benzodiazepine addiction, applicant found subcutaneous infusions to be more practical for long term infusion over many days in patients with poor venous access.

Furthermore, applicant have found in patients with chronic anxiety disorders that continuous infusions of flumazenil with or without the addition of opiate and cannabanoid antagonists is associated with reductions in sleeping pulse rates and marked improvements in the anxiety disorders with these new infusion methods which can be carried out on an outpatient basis for long time periods. The use of flumazenil for treating chronic anxiety disorders has not been described in the past.

Patients with chronic sleep disorders showed good response rates to long term infusions of flumazenil particularly in patients with previous benzodiazepine dependence and chronic anxiety disorders.

Patients with alcohol dependence treated with subcutaneous infusions of flumazenil specifically commented on a reduction in craving for alcohol. In addition, patients with amphetamine dependence reported decreased cravings for amphetamines. These long term outpatient delivery systems, such as the subcutaneous infusion via a pump mechanism or the subcutaneous implant, may be used to control cravings and withdrawal anxiety for amphetamines. Finally, patients with opioid dependence also reported a decreased anxiety and craving after subcutaneous administration of flumazenil using the delivery system of the present invention.

Implant

A subcutaneous implant was designed using polylactic acid and flumazenil to deliver over days or months so that the observed benefits with a constant delivery system in the subcutaneous tissues could be used to achieve the observed benefits noted above. Initial experiments in sheep (>50) confirmed no significant tissue reactions with six months subcutaneous delivery. It was also noted that there was no withdrawal illness when the medication delivery ceased.

Implantable Flumazenil

The implant of the present invention can be prepared by any method capable of producing an implant in a size range acceptable for use in treating a subject. In these methods, the material to be encapsulated (i.e. the active agents) is generally dissolved, dispersed, or emulsified, using known mixing techniques, in a solvent containing the wall-forming material. Solvent is then removed from the microcapsules and thereafter the microcapsule product is obtained. An example of a conventional microencapsulation process is disclosed in U.S. Pat. No. 3,737,337 wherein a solution of a wall or shell forming polymeric material in a solvent is prepared. The solvent is only partially miscible in water. A solid or core material is dissolved or dispersed in the polymer-containing solution and, thereafter, the core-material-containing solution is dispersed in an aqueous liquid that is immiscible in the organic solvent in order to remove solvent from the microcapsules. Another example of a process in which solvent is removed from microcapsules containing a substance is disclosed in U.S. Pat. No. 3,523,906. In this process, a material to be encapsulated is emulsified in a solution of a polymeric material in a solvent that is immiscible in water and then the emulsion is emulsified in an aqueous solution containing a hydrophilic colloid. Solvent removal from the microcapsules is then accomplished by evaporation and the product is obtained. Implants may also be produced according to the methods disclosed in WO 2002/017971.

Clinical work shows that for a flumazenil implant to be effective, the implant should deliver an equivalent dose of 80-250 µg of flumazenil per hour for a continuous period of at least four days. Therefore it is preferable that each tablet comprises 130 mg of flumazenil in a 300 mg tablet, which is designed to release about 1 mg/day of flumazenil with a typical target of at least 100 days of flumazenil delivery. A dose of four tablets would therefore deliver 4 mg per day.

Implants releasing 80-250 µg of flumazenil per hour should partially block receptors for a period of 3 weeks. Thus, the present invention allows flumazenil to be delivered in a reliable fashion for periods greater than four days and preferably greater than three weeks.

Figure 2:
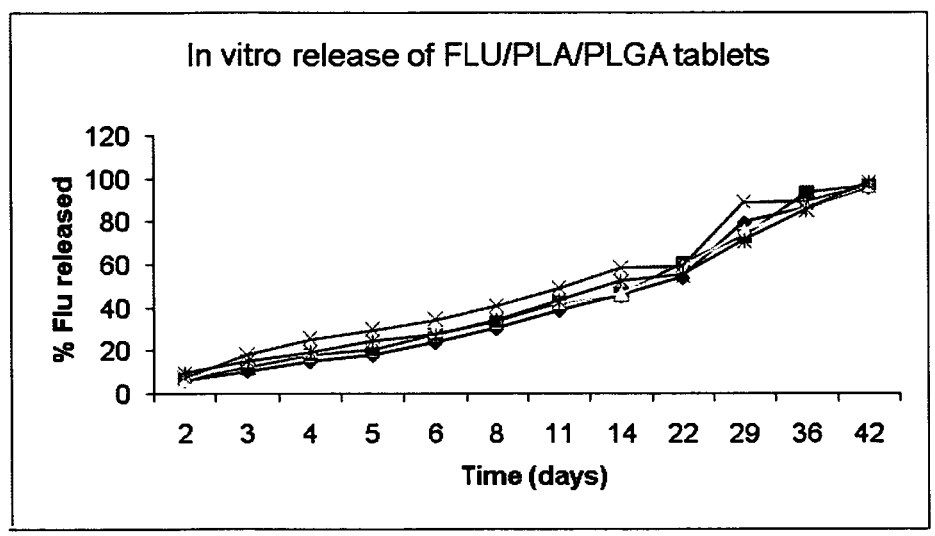
FIG. 2: Graphical representation of flumazenil implant release rates over time.
Figure 3:
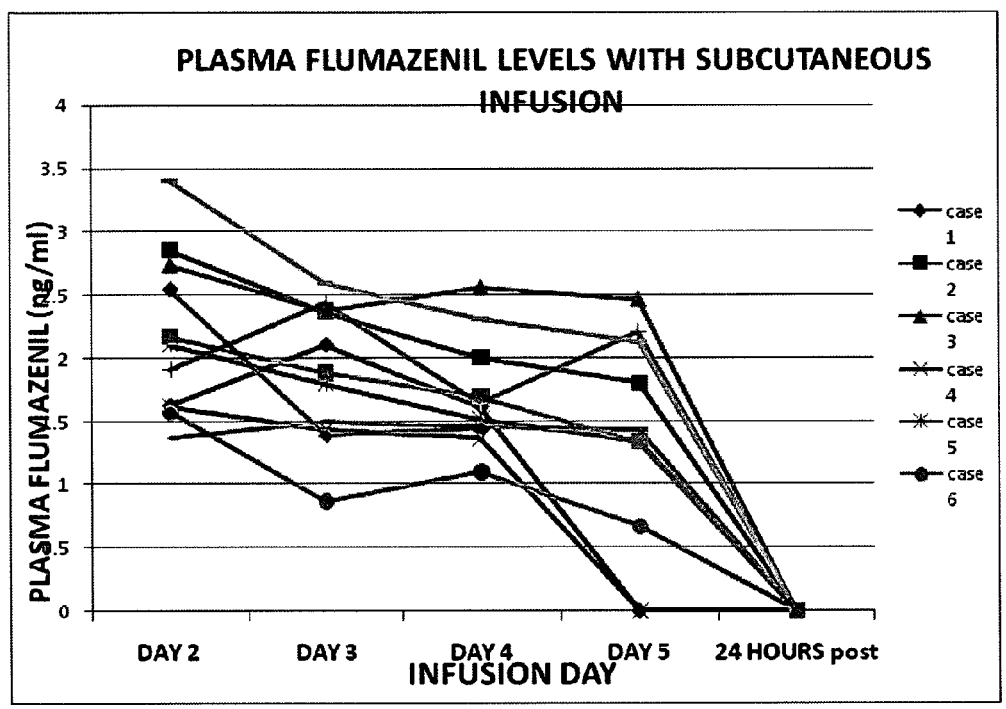
FIG. 3: Graphical representation of plasma flumazenil levels with subcutaneous infusion.

To measure flumazenil in vitro release rates, flumazenil implants were produced according to the present invention. FIG. 2 presents data showing flumazenil released in vitro over 42 days for five separate preparations. Each implant contained 40 mg of flumazenil. Flumazenil levels slowly increased over time at a constant rate to almost 100% by day 42. The data suggests a relative constant release rate of flumazenil from the tablets.

Patients with chronic sleep disorders showed good response rates to long term release of flumazenil from an implant, particularly in patients with previous benzodiazepine dependence and chronic anxiety disorders.

Phase One Study of Flumazenil Implants for the Treatment of Benzodiazepine Dependence Eight volunteers will be assigned to two groups. Group A will be given flumazenil subcutaneous liquid 16 mg/30 over 96 hours (4 mg/day) followed by a flumazenil implant delivering 4 to 8 mg/day for approximately 100 days. Group B will receive only the flumazenil implant. The duration of the study will take place over 18 month time frame.

This study will be conducted in compliance with the protocol approved by Bellberry Human Research Ethics Committee (HREC) according to the ICH Good Clinical Practice Standards. No deviation from the protocol will be implemented without the prior review and approval of the Bellberry HREC except where it may be necessary to eliminate an immediate hazard to a research subject. In such case the deviation will be reported as soon as possible.

Volunteers will be selected on the basis they are dependent on benzodiazepine (daily use greater than 3 months, at greater than 10 mg per day of diazepam equivalents). Men or women aged between 18 and 65 years can be included in the study. Volunteers will have a BMI of between 18.5 to 30 and weigh between 50 to 80 kg for females and between 70 to 100 kg for males.

The primary objection of this study is the collect preliminary data to support future studies on the safety and efficacy of flumazenil implants. In addition, the study aimed to determine the nature, severity and duration of observed and self-reported withdrawal symptoms both during treatment and after cessation of treatment (rebound withdrawal symptoms) and identify patient variables associated with these symptoms. Further, the study aimed to determine the nature and severity of any adverse effects associated with flumazenil and/or the methods of infusion and implantation.

Flumazenil Infusion

The subcutaneous flumazenil infusion used for the initial treatment will be prepared by The Green Dispensary Compounding Pharmacy. The dose is 16 mg flumazenil in 30 ml solution (to be used over 96 hours) and has a pH of 6.8. It will be transferred to a Springfusor for use in patients. The infusion needle is placed in the abdominal area.

Flumazenil Implant

The implant will be manufactured by Go Medical by mixing flumazenil with poly(D,L)lactide to make microspheres, compressed into tablets and spray-coated with poly(D,L)lactide solution to create controlled release. Ten tablets will be collected into a delivery syringe and will comprise 1 implant. The implants will be tested in a water bath to ensure that the flumazenil release rate per day is between 4 and 8 mg/day.

Dosage

In this particular study, each subject will receive a subcutaneous infusion dose and an implanted sustained-release dose. The prepared dose will deliver 4 mg of flumazenil per 24-hour period for 96 hours. However if the patient's body mass is higher than average (e.g. greater than 50-80 kg for females or 70-100 kg for males) two prepared doses will be used to make 8 mg/24 hours. The subcutaneous infusion will serve to confirm that the dose chosen will suit the patient's treatment needs before implantation. The dose of the implant may be varied by inserting one or two implants to make up the required dose. The aim of the dosage is to ensure that 2-3% of the benzodiazepine sites are occupied by flumazenil.

The data supporting the development of a sustained release flumazenil implant is strong. The inadequate clinical outcomes of benzodiazepine tapering as well as drawbacks of intravenous flumazenil (such as the low pH) are documented in the literature. Clinical experience of anxiety following the end of 4-day infusions and relapse to benzodiazepine dependence afterwards, together with research confirming the existence of a prolonged benzodiazepine withdrawal syndrome suggest that a much longer term, reliable pharmacotherapy with one-time patient compliance requirements would benefit a large number of benzodiazepine-dependent patients. Positive experience of the O'Neil Long Acting Naltrexone Implant in heroin-dependent patients indicates that the delivery method of a poly-(D,L)lactide-based implant is effective, acceptable and safe and that a pharmacotherapy delivery period of 100 days is well within the range of possibilities.

Study Protocol

Eight benzodiazepine-dependent subjects will be recruited for this study. The first four patients to enroll in the study will form Group A. Volunteers in Group A will receive a flumazenil infusion of 4 to 8 mg/day for 4 days (96 hours), following which they will receive a flumazenil implant at matched dose, designed to be active for 100 days. During the first four weeks of active implant, weekly interviews will be conducted with the patients to assess any side effects and craving ratings will be accessed. Subsequently, patients will be asked to provide interviews every four weeks for the following 84 days.

Due to the need to assess Group A's treatment regime before starting Group B, if volunteers choose to discontinue the study before receiving the flumazenil implant, further Group A volunteers will be recruited to make a total of 4 volunteers receiving the Group A implant treatment before the Group B phase begins.

The next four volunteers will form Group B. Group B volunteers will not receive an initial infusion but will receive a flumazenil implant of 4 to 8 mg/day is designed to be active for 100 days. No volunteers in Group B will start treatment until all the Group A volunteers have completed four weeks from the time of implant. As with Group A, weekly interviews for four weeks and four-weekly interviews for the next 84 days will be conducted.

Volunteers presenting with daily benzodiazepine use greater than 10 mg day diazepam equivalent for more than the previous three months, and wishing to withdraw from and cease using benzodiazepine, who consent to participate in the study and meet the study's inclusion and exclusion criteria will be eligible for the study. If the volunteer meets the criteria they will be invited to meet with a study doctor to discuss the study and their participation. During the interview, the doctor will thoroughly discuss the study protocol, requirements of participants, data collection. If the participant is still interested in participating in the study a blood sample will be collected for Liver Function Test (LFT), Full Blood Examination (FBE), Urea and Electrolytes (U&E), Hepatitis A, B and C serology, HIV and syphilis serology and urine will be collected for urinalysis, pregnancy test and drug urine screen. The results of these will then be used to ensure the volunteer doesn't have any underlying problems that may affect the study or exclude them from participating such as pregnancy, abnormal liver function or current opiate use. If the volunteer meets the criteria and is still willing to participate in the study, they will be invited to sign the consent forms, before being enrolled on to the study. A total of eight patients will be enrolled into the study.

On day 1, prior to commencement of flumazenil infusion baseline data will be collected on demographics, drug use history, physical examination, urine drug screen and measures of addiction severity, personality assessment, psychological and social functioning. Treatment will begin immediately after collection of baseline data.

The flumazenil solution will be supplied by Go Medical Industries Pty Ltd. Each ampoule of solution contains 16 mg of flumazenil in 30 ml saline solution. The solution and ampoules will be sterilized by autoclave. Labelling will be as per GMP Annex 13 requirements.

Group A: subjects will be treated with a subcutaneous flumazenil infusion (pH 6.8). Subcutaneous flumazenil infusion will be administered via a Springfusor® syringe infusion pump device developed by Go Medical Industries, Australia. The Springfusor® infusion pump is attached via butterfly needle inserted on the anterior abdominal wall or other selected site, and worn on a belt pouch. The dose of flumazenil administered will be 4 mg/24 hours (±20%) for a period of 96 hours. Patients will be housed in Fresh Start Recovery Programme's medically supervised accommodation for the 96 hours of infusion.

At the end of the 96-hour infusion period data will be collected on withdrawal effects and any adverse reactions to the flumazenil infusion, and the physical examination, urine drug screen and measures of addiction severity, personality assessment, psychological and social functioning will be repeated. The examining physician will assess the dose level and decide whether a dose adjustment needs to be made in the next phase. The design and activity of the implant will be explained fully to the patient for a second time and the patient will be given time to ask questions before giving consent to continue.

If the patient consents and to having a flumazenil implant which is designed to be active for 100 days, and if no adverse events or changes in circumstances have occurred which mean the examining physician wishes to discontinue the patient's involvement in the study, the patient will be implanted with a flumazenil implant on the same day. If either the patient does not consent or the physician wishes the patient to discontinue the study, the reasons for any discontinuation will be recorded and the patient will take no further part in the study.

Immediately after the assessment and consent to continue in the study have been progressed, Group A patients will be invited to receive flumazenil implant(s) suitable for the dose which was indicated from the infusion phase. Group B patients will begin the study at this stage.

The implant will be inserted under the skin through a small cut made in the subcutaneous tissue, usually below the belt line, under local anaesthetic and the cut sealed with medical glue or a few stitches.

The patient will be housed in Fresh Start Recovery Programme's medically supervised accommodation for the first 96 hours after receiving the implant. In cases where no stable and suitable home environment exists (unsuitable environments can include sharing a home with current drug users), the patient will then be offered the possibility of staying at Fresh Start Recovery Programme's rehabilitation centre for 6 months.

Data Collection

Any adverse events (such as untoward medical occurrence in a patient or clinical investigational subject administered a pharmaceutical product and which does not necessarily have a causal relationship with this treatment) and serious adverse events (such as adverse experience occurring during the study period that: results in death; is life-threatening; results in inpatient hospitalisation or prolongation of existing hospitalisation; or results in a persistent or significant disability/incapacity; or results in congenital anomaly/birth defect) information will be reviewed by a data monitoring committee (DMC) constituted similarly or with equivalence to a DMC previously established for a clinical trial with the same investigational product. This comprised a Professor of Psychiatry, Professor of Public Health, and two Addiction Specialists who were fellows of the Australasian College of Addiction Medicine. The DMC will make the final decision on whether the event is "unexpected", "expected", "pre-existing" or "unrelated" based on the Therapeutic Goods Administration algorithm. These guidelines are based on the relevant International Conference on Harmonisation policies. A final document detailing all study-related adverse events classified as "unexpected", "expected", "pre-existing" (i.e. present at the time of enrolment), or "unrelated" will be produced. This document will be submitted to Bellberry HREC and to Go Medical for update of the Investigational Brochure.

A charter will be established outlining the function, operations and reporting function of the DMC based on the international guidelines on the functions of data monitoring committees[i]. The DMC may contact the investigator to request more information about a specific event, in order to properly classify the event.

The DMC review of safety data is additional to the Investigator's reporting requirements for adverse events, which are described at 8.3. The investigator's initial assessment of treatment causality may later be reviewed and revised by the DMC.

Benefits of Treatment

1. The development of a subcutaneous sustained release of flumazenil preparation has the potential to greatly improve the way in which benzodiazepine dependent persons are treated.
2. benzodiazepine dependence places great pressure on society, especially the justice, welfare and public hospital systems, and costs the public billions. Flumazenil implants have the potential to combat benzodiazepine dependence, thus can make a huge difference to the individual involved, as well as society as a whole.
3. The use of flumazenil has also shown some efficacy in the treatment of alcoholism and amphetamine dependence which could both be improved by the use of a long acting flumazenil preparation.
4. Subjects may feel they are making a worthwhile contribution to the area of addiction treatment research, and helping out their community.

Patient Controlled Delivery Systems

It was also found that the solution of flumazenil at a concentration of about 0.5 mg/ml to 0.6 mg/ml at a pH of between 6.5 to 7.0 was suitable for self administration by subjects. Subjects that were treated by this method included subjects suffering from anxiety and patients with cravings for addictive substances.

Nasal Spray

A nasal delivery system was devised for the delivery of flumazenil either alone or in combination with one or more active agents. A pulsatile or burst delivery of flumazenil with or without the addition of one or more active agents can be used to control smoking and most likely other addictions.

In one experiment, flumazenil and naltrexone were mixed to capture the benefits of mixing a benzodiazepine antagonist and an opiate antagonist to be given in a pulsative manner when cravings were observed. This formulation and delivery system was used successfully to assist a patient on 25 cigarettes per day to stop the same day that she commenced the mixture nasally when craving episodes occurred. Additional patients have been tested with similar results.

Thus, we observed the delivery of flumazenil and the opiate antagonist, with pulsatile micro-dose delivery on a patient controlled basis to be effective in smoking controlled symptoms and patient controlled anxiety. We have also noted that the patient controlled delivery of flumazenil or opiate antagonist alone to also decrease symptoms of craving and anxiety. These observations have not been made before and we believe this introduces a new treatment technique for smoking control.

Nasal doses of flumazenil in micro-doses (50 micrograms, normally considered to be non-therapeutic) were combined with micro-doses of another opioid (e.g. naltrexone 50 micrograms) or cannabanoid antagonist we observed a decreased craving for smoking which appeared to be greater than for opioid antagonist alone or flumazenil alone. Thus, the author observed a synergistic effect which controlled symptoms. To the author's knowledge, these findings have not previously been reported.

In some instances, the patient is capable of self administering an active agent, such as flumazenil or a mixture of flumazenil and one or more active agents. For example, a low dose by bolus delivery of the active agent(s) across the nasal mucosa, as discussed above may be used by a patient to self medicate.

Subcutaneous Delivery

In addition to delivery of flumazenil across the nasal membrane, the inventors showed that subcutaneous bolus doses of flumazenil in the order of 10-200 micrograms as required for symptom control by the patient may be self administered. The use of micro-doses of flumazenil (less than 200 micrograms) given on a patient controlled basis has not previously been described. In addition, the use of micro-doses with a patient activated pump has not previously been described.

Figure 4:
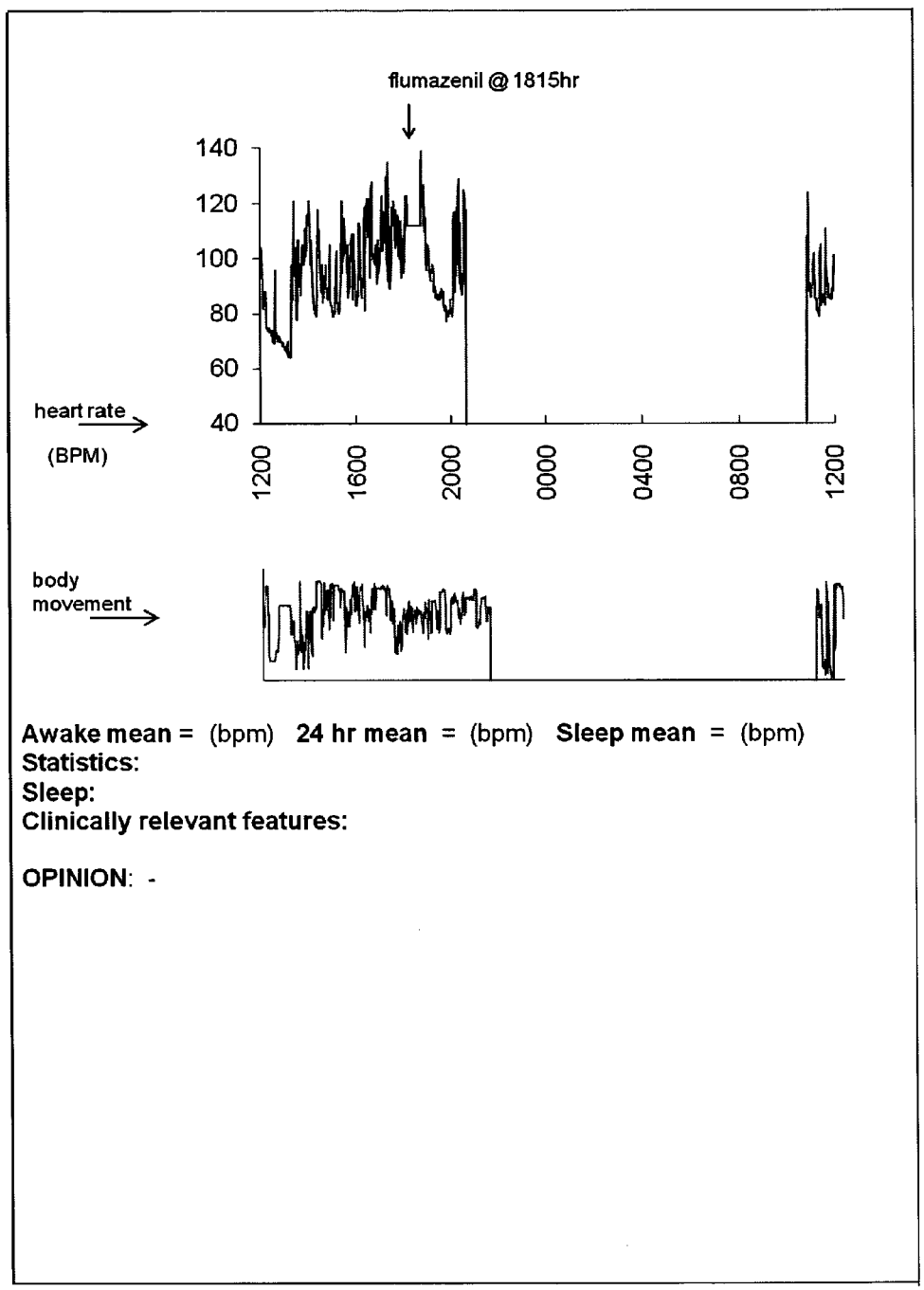
FIG. 4: Graphical representation of the heart rate and body movement of a patient prior to, during and after a single dose of flumazenil administered via a patient controlled pump.

In one study we showed that 1 mg of flumazenil delivered via subcutaneously pump allowed the control of anxiety as evidenced by the decrease in pulse rate (see FIG. 4) and other signs and symptoms of anxiety. The heart rate and the body movement of the patient were recorded using standard equipment. A single dose of flumazenil was administered at 6:15 pm and was followed by a reduction in pulse rate, which reflected a decrease in anxiety state. The heart rate changes on the graph show a drop in pulse rate from close to 120 beats per minute (bpm) to 80 bpm in the 60 minutes following a single subcutaneous delivery in the patient suffering from chronic anxiety. This single dose administered by a patent controlled delivery of flumazenil was associated with a reduction in anxiety as required in stressful settings.

This data supports our previously observed findings that flumazenil and most likely other benzodiazepine antagonists can be used to control anxiety. The gradual correction of anxiety disorders occurs with flumazenil delivery over days or weeks. The self administered subcutaneous injections represent a counter intuitive discovery that an antagonist can be used to control performance anxiety.

This is counter intuitive as the use of an agonist at the benzodiazepine receptor to control performance anxiety is well known and experts in the field would find it unexpected to see that we are now offering patients an antagonist to the benzodiazepine receptor to control performance and other anxiety through subcutaneous delivery (or nasal spray or patch) delivered by patients controlling their own anxiety symptoms. The innovative treatment offers the first patient activated treatment system for anxiety control which is non addictive and does not decrease cognitive function. All other medications available would decrease cognitive function.

Delivery Across the Skin

The most common approach to delivering a substance across the skin is via patch or cream. The flumazenil solution of between 0.5 mg/ml to 0.6 mg/ml may be used to prepare a preparation that delivers flumazenil across the skin, in such an amount of flumazenil to maintain a continuous administration 40 µg to 1000 µg of flumazenil to the subject in need of treatment thereof.

The claims defining the invention are as follows:

1. A method for treating benzodiazepine overdose in a human subject in need thereof, the method consisting of a) providing a preparation consisting of flumazenil as its sole active agent, and b) administering the preparation as a single dose to a human subject to provide flumazenil at a continuous rate of between 40 µg/h to 1000 µg/h over a period of time of greater than four days.

2. The method according to claim 1, wherein the flumazenil is provided at a concentration of between 0.11 to 0.7 mg/ml prepared in saline at a pH between pH 6.5 to 7.0.

3. The method according to claim 1, wherein the flumazenil is adapted to be delivered via subcutaneous implant.

4. The method according to claim 1, wherein the flumazenil is delivered at a continuous rate of between 80 µg/h to 250 µg/h.

5. The method according to claim 1 wherein the flumazenil is delivered continuously to a human subject over a period of sixteen days or more.

6. The method according to claim 1, wherein the flumazenil is provided at a concentration of between 0.11 to 0.7 mg/ml prepared in saline at a pH between pH 6.5 to 7.0, and the flumazenil is adapted to be delivered via subcutaneous implant.

7. The method according to claim 1, wherein the flumazenil is provided at a concentration of between 0.11 to 0.7 mg/ml prepared in saline at a pH between pH 6.5 to 7.0, and the flumazenil is delivered at a continuous rate of between 80 µg/h to 250 µg/h.

8. The method according to claim 1, wherein the flumazenil is adapted to be delivered via subcutaneous implant and is delivered continuously to a human subject over a period of sixteen days or more.

9. The method according to claim 1, wherein the flumazenil is adapted to be delivered via subcutaneous implant, and is delivered at a continuous rate of between 80 µg/h to 250 µg/h.

10. The method according to claim 1, wherein the flumazenil is adapted to be delivered via subcutaneous implant, the flumazenil is delivered at a continuous rate of between 80 µg/h to 250 µg/h, and the flumazenil is delivered continuously to a human subject over a period of sixteen days or more.

11. The method according to claim 1, wherein the flumazenil is provided at a concentration of between 0.11 to 0.7 mg/ml prepared in saline at a pH between pH 6.5 to 7.0, the flumazenil is adapted to be delivered via subcutaneous implant, the flumazenil is delivered at a continuous rate of between 80 µg/h to 250 µg/h, and the flumazenil is delivered continuously to a human subject over a period of sixteen days or more.

12. The method according to claim 1, wherein the flumazenil is provided at a concentration of between 0.11 to 0.7 mg/ml prepared in saline at a pH between pH 6.5 to 7.0, and the flumazenil is delivered continuously to a human subject over a period of sixteen days or more.

* * * * *